US008617193B2

(12) United States Patent
Wu

(10) Patent No.: US 8,617,193 B2
(45) Date of Patent: Dec. 31, 2013

(54) BALLOON CATHETER WITH IMPROVED PUSHABILITY

(75) Inventor: Show-Mean Wu, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/464,407

(22) Filed: May 4, 2012

(65) Prior Publication Data
US 2012/0220935 A1    Aug. 30, 2012

Related U.S. Application Data

(63) Continuation of application No. 12/638,318, filed on Dec. 15, 2009, now Pat. No. 8,172,864, which is a continuation of application No. 10/436,216, filed on May 12, 2003, now Pat. No. 7,632,288.

(51) Int. Cl.
*A61B 17/22* (2006.01)
(52) U.S. Cl.
USPC ............................. 606/159; 606/194; 604/524
(58) Field of Classification Search
USPC .............. 606/108, 159, 170, 191, 192, 194; 604/103.04, 96, 102.02, 523, 524
See application file for complete search history.

(56) References Cited

U.S. PATENT DOCUMENTS

| | | | |
|---|---|---|---|
| 2,816,552 A | 12/1957 | Hoffman | |
| 3,174,851 A | 3/1965 | Buehler et al. | |
| 3,351,463 A | 11/1967 | Rozner et al. | |
| 3,635,223 A | 1/1972 | Klieman | |
| 3,749,085 A | 7/1973 | Willson et al. | |
| 3,753,700 A | 8/1973 | Harrison et al. | |
| 3,990,453 A | 11/1976 | Douvas et al. | |
| 4,140,126 A | 2/1979 | Choudhury | |
| 4,141,364 A | 2/1979 | Schultze | |
| 4,263,236 A | 4/1981 | Briggs et al. | |
| 4,273,128 A | 6/1981 | Lary | |

(Continued)

FOREIGN PATENT DOCUMENTS

DE    31 24 198 A1    4/1982
DE    34 00 416 A1    7/1985

(Continued)

OTHER PUBLICATIONS

Lary, Banning G., et al., "A Method for Creating a Coronary-Myocardial Artery," *Surgery*, Jun. 1966, vol. 59, No. 6, pp. 1061-1064.

(Continued)

*Primary Examiner* — Tuan V Nguyen
(74) *Attorney, Agent, or Firm* — Seager, Tufte & Wickhem, LLC

(57) ABSTRACT

Rapid exchange angioplasty catheters and methods of constructing rapid exchange angioplasty catheters including features that provide good pushability and kink resistance. In an illustrative embodiment, a catheter is provided, the illustrative catheter including a proximal hypotube section, which connects to a more distal braided catheter section. The braided catheter section connects to a midshaft portion that includes a guidewire entry port. Distal of the midshaft portion is a distal section having a balloon disposed thereon. An inflation lumen extends the length of the catheter, while a guidewire lumen extends only from the guidewire entry port to the distal end of the catheter. Optionally, a core wire may extend across the joint from the hypotube, to the braided catheter section, and past the guidewire entry port.

9 Claims, 7 Drawing Sheets

(56) References Cited

U.S. PATENT DOCUMENTS

| | | |
|---|---|---|
| 4,292,974 A | 10/1981 | Fogarty et al. |
| 4,406,656 A | 9/1983 | Hattler et al. |
| 4,465,072 A | 8/1984 | Taheri |
| 4,490,421 A | 12/1984 | Levy |
| 4,572,186 A | 2/1986 | Gould et al. |
| 4,574,781 A | 3/1986 | Chin |
| 4,608,984 A | 9/1986 | Fogarty |
| 4,627,436 A | 12/1986 | Leckrone |
| 4,685,458 A | 8/1987 | Leckrone |
| 4,686,982 A | 8/1987 | Nash |
| 4,696,667 A | 9/1987 | Masch |
| 4,705,517 A | 11/1987 | DiPisa, Jr. |
| 4,723,549 A | 2/1988 | Wholey et al. |
| 4,728,319 A | 3/1988 | Masch |
| 4,747,405 A | 5/1988 | Leckrone |
| 4,748,982 A | 6/1988 | Horzewski et al. |
| 4,781,186 A | 11/1988 | Simpson et al. |
| 4,784,636 A | 11/1988 | Rydell |
| 4,787,388 A | 11/1988 | Hofmann |
| 4,790,813 A | 12/1988 | Kensey |
| 4,793,348 A | 12/1988 | Palmaz |
| 4,796,629 A | 1/1989 | Grayzel |
| 4,799,479 A | 1/1989 | Spears |
| RE32,983 E | 7/1989 | Levy |
| 4,867,157 A | 9/1989 | McGurk-Burleson et al. |
| 4,886,061 A | 12/1989 | Fischell et al. |
| 4,896,669 A | 1/1990 | Bhate et al. |
| 4,909,781 A | 3/1990 | Husted |
| 4,921,483 A | 5/1990 | Wijay et al. |
| 4,921,484 A | 5/1990 | Hillstead |
| 4,936,845 A | 6/1990 | Stevens |
| 4,960,410 A | 10/1990 | Pinchuk |
| 4,966,604 A | 10/1990 | Reiss |
| 4,986,807 A | 1/1991 | Farr |
| 4,994,018 A | 2/1991 | Saper |
| RE33,561 E | 3/1991 | Levy |
| 5,009,659 A | 4/1991 | Hamlin et al. |
| 5,015,231 A | 5/1991 | Keith et al. |
| 5,030,201 A | 7/1991 | Palestrant |
| 5,041,125 A | 8/1991 | Montano, Jr. |
| 5,042,985 A | 8/1991 | Elliott et al. |
| 5,047,040 A | 9/1991 | Simpson et al. |
| 5,053,007 A | 10/1991 | Euteneuer |
| 5,053,044 A | 10/1991 | Mueller et al. |
| 5,071,424 A | 12/1991 | Reger |
| 5,074,841 A | 12/1991 | Ademovic et al. |
| 5,074,871 A | 12/1991 | Groshong |
| 5,078,722 A | 1/1992 | Stevens |
| 5,078,725 A | 1/1992 | Enderle et al. |
| 5,084,010 A | 1/1992 | Plaia et al. |
| 5,085,662 A | 2/1992 | Willard |
| 5,087,246 A | 2/1992 | Smith |
| 5,087,265 A | 2/1992 | Summers |
| 5,100,424 A | 3/1992 | Jang et al. |
| 5,100,425 A | 3/1992 | Fischell et al. |
| 5,102,390 A | 4/1992 | Crittenden et al. |
| 5,102,403 A | 4/1992 | Alt |
| 5,116,318 A | 5/1992 | Hillstead |
| 5,135,482 A | 8/1992 | Neracher |
| 5,147,302 A | 9/1992 | Euteneuer et al. |
| 5,152,773 A | 10/1992 | Redha |
| 5,156,594 A | 10/1992 | Keith |
| 5,156,610 A | 10/1992 | Reger |
| 5,158,564 A | 10/1992 | Schnepp-Pesch et al. |
| 5,176,693 A | 1/1993 | Pannek, Jr. |
| 5,178,625 A | 1/1993 | Groshong |
| 5,180,368 A | 1/1993 | Garrison |
| 5,192,291 A | 3/1993 | Pannek, Jr. |
| 5,196,024 A | 3/1993 | Barath |
| 5,196,025 A | 3/1993 | Ranalletta et al. |
| 5,209,749 A | 5/1993 | Buelna |
| 5,209,799 A | 5/1993 | Vigil |
| 5,226,430 A | 7/1993 | Spears et al. |
| 5,226,887 A | 7/1993 | Farr et al. |
| 5,226,909 A | 7/1993 | Evans et al. |
| 5,242,396 A | 9/1993 | Evard |
| 5,248,311 A | 9/1993 | Black et al. |
| 5,250,059 A | 10/1993 | Andreas et al. |
| 5,295,959 A | 3/1994 | Gurbel et al. |
| 5,300,025 A | 4/1994 | Wantink |
| 5,312,425 A | 5/1994 | Evans et al. |
| 5,318,576 A | 6/1994 | Plassche, Jr. et al. |
| 5,320,634 A | 6/1994 | Vigil et al. |
| 5,328,472 A | 7/1994 | Steinke et al. |
| 5,336,234 A | 8/1994 | Vigil et al. |
| 5,342,301 A | 8/1994 | Saab |
| 5,342,307 A | 8/1994 | Euteneuer et al. |
| 5,346,505 A | 9/1994 | Leopold |
| 5,350,361 A | 9/1994 | Tsukashima et al. |
| 5,372,601 A | 12/1994 | Lary |
| 5,395,361 A | 3/1995 | Fox et al. |
| 5,399,164 A | 3/1995 | Snoke et al. |
| 5,403,334 A | 4/1995 | Evans et al. |
| 5,409,454 A | 4/1995 | Fischell et al. |
| 5,411,466 A | 5/1995 | Hess |
| 5,411,478 A | 5/1995 | Stillabower |
| 5,415,654 A | 5/1995 | Daikuzono |
| 5,417,653 A | 5/1995 | Sahota et al. |
| 5,417,703 A | 5/1995 | Brown et al. |
| 5,423,745 A | 6/1995 | Todd et al. |
| 5,425,711 A | 6/1995 | Ressemann et al. |
| 5,425,712 A | 6/1995 | Goodin |
| 5,437,659 A | 8/1995 | Leckrone |
| 5,441,510 A | 8/1995 | Simpson et al. |
| 5,449,343 A | 9/1995 | Samson et al. |
| 5,456,666 A | 10/1995 | Campbell et al. |
| 5,456,681 A | 10/1995 | Hajjar |
| 5,458,572 A | 10/1995 | Campbell et al. |
| 5,478,319 A | 12/1995 | Campbell et al. |
| 5,487,730 A | 1/1996 | Marcadis et al. |
| 5,496,308 A | 3/1996 | Brown et al. |
| 5,507,760 A | 4/1996 | Wynne et al. |
| 5,507,761 A | 4/1996 | Duer |
| 5,522,818 A | 6/1996 | Keith et al. |
| 5,522,825 A | 6/1996 | Kropf et al. |
| 5,538,510 A | 7/1996 | Fontirroche et al. |
| 5,549,556 A | 8/1996 | Ndondo-Lay et al. |
| 5,554,121 A | 9/1996 | Ainsworth et al. |
| 5,556,405 A | 9/1996 | Lary |
| 5,556,408 A | 9/1996 | Farhat |
| 5,569,277 A | 10/1996 | Evans et al. |
| 5,571,087 A | 11/1996 | Ressemann et al. |
| 5,616,149 A | 4/1997 | Barath |
| 5,628,761 A | 5/1997 | Rizik |
| 5,643,209 A | 7/1997 | Fugoso et al. |
| 5,643,296 A | 7/1997 | Hundertmark et al. |
| 5,649,941 A | 7/1997 | Lary |
| 5,662,671 A | 9/1997 | Barbut et al. |
| 5,669,920 A | 9/1997 | Conley et al. |
| 5,681,336 A | 10/1997 | Clement et al. |
| 5,697,944 A | 12/1997 | Lary |
| 5,713,913 A | 2/1998 | Lary et al. |
| 5,718,684 A | 2/1998 | Gupta |
| 5,720,724 A | 2/1998 | Ressemann et al. |
| 5,728,123 A | 3/1998 | Lemelson et al. |
| 5,743,875 A | 4/1998 | Sirhan et al. |
| 5,759,191 A | 6/1998 | Barbere |
| 5,769,819 A | 6/1998 | Schwab et al. |
| 5,769,865 A | 6/1998 | Kermode et al. |
| 5,792,158 A | 8/1998 | Lary |
| 5,797,935 A | 8/1998 | Barath |
| 5,800,450 A | 9/1998 | Lary et al. |
| 5,820,594 A | 10/1998 | Fontirroche et al. |
| 5,824,173 A | 10/1998 | Fontirroche et al. |
| 5,827,201 A | 10/1998 | Samson et al. |
| 5,827,225 A | 10/1998 | Ma Schwab |
| 5,827,310 A | 10/1998 | Marin et al. |
| 5,895,402 A | 4/1999 | Hundertmark et al. |
| 5,921,958 A | 7/1999 | Ressemann et al. |
| 5,931,819 A | 8/1999 | Fariabi |
| 5,993,469 A | 11/1999 | McKenzie et al. |
| 5,997,557 A | 12/1999 | Barbut et al. |
| 6,010,521 A | 1/2000 | Lee et al. |
| 6,024,722 A | 2/2000 | Rau et al. |

(56) References Cited

U.S. PATENT DOCUMENTS

| | | |
|---|---|---|
| 6,030,371 A | 2/2000 | Pursley |
| 6,039,699 A | 3/2000 | Viera |
| 6,066,149 A | 5/2000 | Samson et al. |
| 6,068,623 A | 5/2000 | Zadno-Azizi et al. |
| 6,110,192 A | 8/2000 | Ravenscroft et al. |
| 6,117,153 A | 9/2000 | Lary et al. |
| 6,139,510 A | 10/2000 | Palermo |
| 6,142,975 A | 11/2000 | Jalisi et al. |
| 6,165,140 A | 12/2000 | Ferrera |
| 6,165,167 A | 12/2000 | Delaloye |
| 6,165,292 A | 12/2000 | Abrams et al. |
| 6,168,571 B1 | 1/2001 | Solar et al. |
| 6,179,851 B1 | 1/2001 | Barbut et al. |
| 6,190,332 B1 | 2/2001 | Muni et al. |
| 6,193,686 B1 | 2/2001 | Estrada et al. |
| 6,213,957 B1 | 4/2001 | Milliman et al. |
| 6,217,549 B1 | 4/2001 | Selmon et al. |
| 6,217,567 B1 | 4/2001 | Zadno-Azizi et al. |
| 6,221,006 B1 | 4/2001 | Dubrul et al. |
| 6,241,690 B1 | 6/2001 | Burkett et al. |
| 6,254,550 B1 | 7/2001 | McNamara et al. |
| 6,258,108 B1 | 7/2001 | Lary |
| 6,283,743 B1 | 9/2001 | Traxler et al. |
| 6,306,105 B1 | 10/2001 | Rooney et al. |
| 6,306,151 B1 | 10/2001 | Lary |
| 6,309,399 B1 | 10/2001 | Barbut et al. |
| 6,344,029 B1 | 2/2002 | Estrada et al. |
| 6,355,016 B1 | 3/2002 | Bagaoisan et al. |
| 6,361,529 B1 | 3/2002 | Goodin et al. |
| 6,383,146 B1 | 5/2002 | Klint |
| 6,387,075 B1 | 5/2002 | Stivland et al. |
| 6,394,995 B1 | 5/2002 | Solar et al. |
| 6,398,798 B2 | 6/2002 | Selmon et al. |
| 6,409,863 B1 | 6/2002 | Williams et al. |
| 6,425,882 B1 | 7/2002 | Vigil |
| 6,471,673 B1 | 10/2002 | Kasterhofer |
| 6,471,713 B1 | 10/2002 | Vargos et al. |
| 6,533,754 B1 | 3/2003 | Hisamatsu et al. |
| 6,544,276 B1 | 4/2003 | Azizi |
| 6,562,022 B2 | 5/2003 | Hoste et al. |
| 6,562,062 B2 | 5/2003 | Jenusaitis et al. |
| 6,602,265 B2 | 8/2003 | Dubrul et al. |
| 6,632,231 B2 | 10/2003 | Radisch, Jr. |
| 8,172,864 B2 * | 5/2012 | Wu .............................. 606/159 |
| 2002/0010489 A1 | 1/2002 | Grayzel et al. |
| 2003/0163148 A1 | 8/2003 | Wang et al. |
| 2003/0208222 A1 | 11/2003 | Zadno-Azizi |

FOREIGN PATENT DOCUMENTS

| | | |
|---|---|---|
| DE | 34 02 573 | 8/1985 |
| DE | 35 19 626 A1 | 12/1986 |
| EP | 0 291 170 A1 | 11/1988 |
| EP | 0 414 350 A1 | 2/1991 |
| EP | 0 784 966 B1 | 7/1997 |
| EP | 0 792 656 A1 | 9/1997 |
| GB | 1 547 328 | 6/1979 |
| GB | 2078114 A | 1/1982 |
| WO | WO 90/07909 A1 | 7/1990 |
| WO | WO 91/17714 A1 | 11/1991 |
| WO | WO 01/70323 A1 | 9/2001 |
| WO | WO 01/95973 A2 | 12/2001 |

OTHER PUBLICATIONS

Lary, Banning G., "A Method to Create and Correct Stenosis of a Coronary Artery," *Archives of Surgery*, Nov. 1966, vol. 93, pp. 828-830.

Lary, Banning G., "An Epicaridal Purse String Suture for Closing Coronary Arteriotomy," *The American Surgeon*, Mar. 1967, vol. 33, No. 3, pp. 213-214.

Lary, Banning G., "Coronary Artery Incision and Dilation," *Archives of Surgery*, Dec. 1980, vol. 115, pp. 1478-1480.

Lary, Banning G., "Coronary Artery Resection and Replacement by a Blood Conduit," *Surgery*, Apr. 1969, vol. 65, No. 4, pp. 584-589.

Lary, Banning G., "Effect of Endocardial Incisions on Myocardial Blood Flow," *Archives of Surgery*, Sep. 1963, vol. 87, pp. 424-427.

Lary, B.G., "Experimental Maintenance of Life by Intravenous Oxygen, Preliminary Report," *Clinical Congress of the American College of Surgeons*, San Francisco, Nov. 5-9, 1951, pp. 30-35.

Lary, Banning G., et al., "Experimental Vein Angioplasty of the Circumflex Coronary Artery," *Journal of Surgical Research*, Sep. 1974, vol. 17, No. 3, pp. 210-214.

Lary, Banning G., "Method for Increasing the Diameter of Long Segments of the Coronary Artery," *The American Surgeon*, Jan. 1966, vol. 32, No. 1, pp. 33-35.

Lary, Banning G., et al., "Myocardial Revascularization Experiments Using the Epicardium," *Archives of Surgery*, Jan. 1969, vol. 98, pp. 69-72.

Lary, Banning G., "Onlay Vein Graft for the Correction of Coronary Artery Obstruction," *Surgery*, Apr. 1966, vol. 59, No. 4, pp. 547-551.

Lary, Banning G., "Surgery for Coronary Artery Disease," *Nursing Clinics of North America*, Sep. 1967, vol. 2, No. 3, pp. 537-542.

Lary, Banning G., et al., "The 'Coronary Myocardial Artery' for Coronary Artery Disease," *Diseases of the Chest*, Apr. 1996, vol. 49, No. 4, pp. 412-419.

* cited by examiner

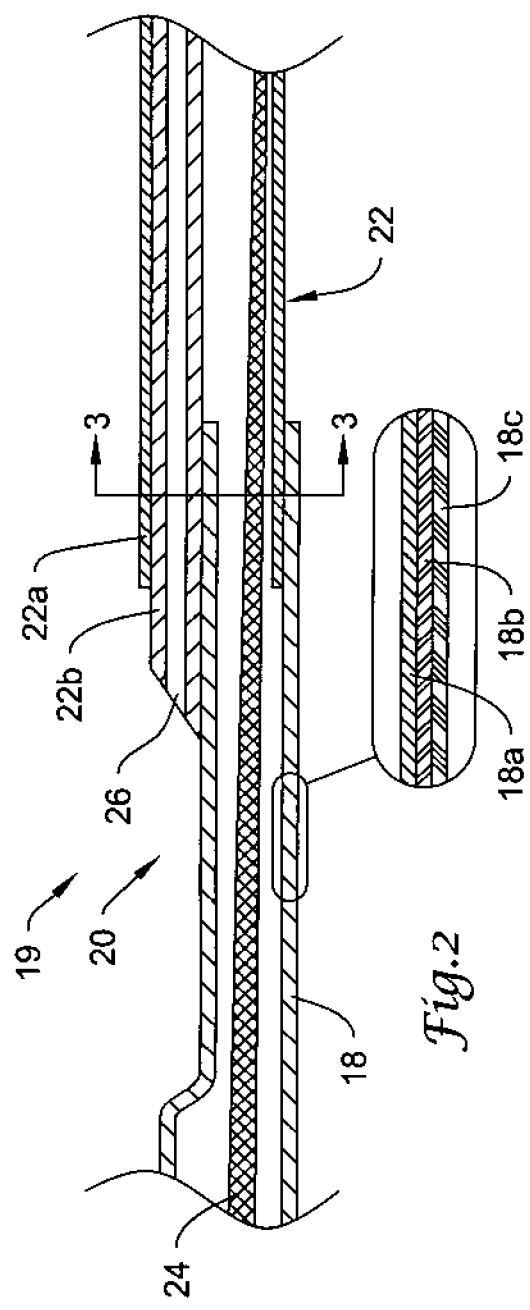
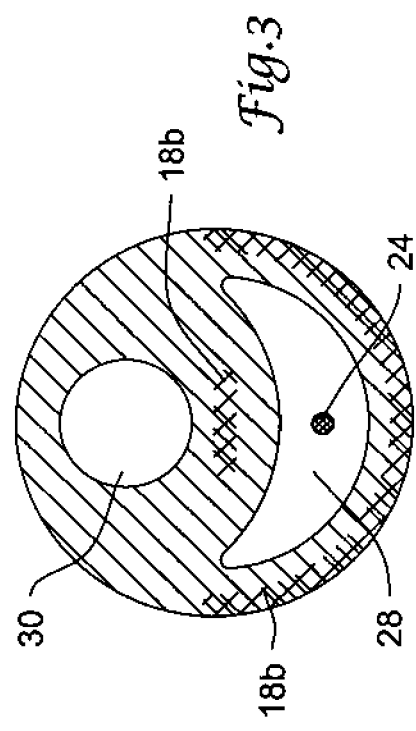

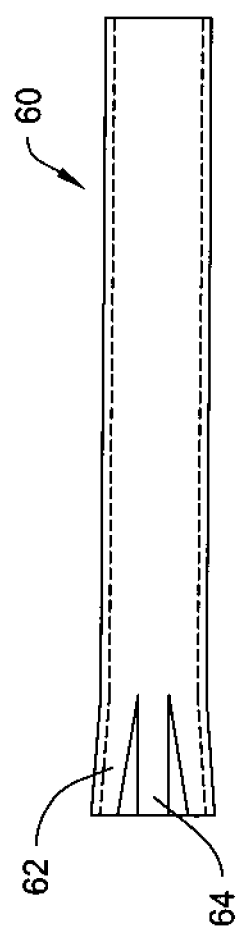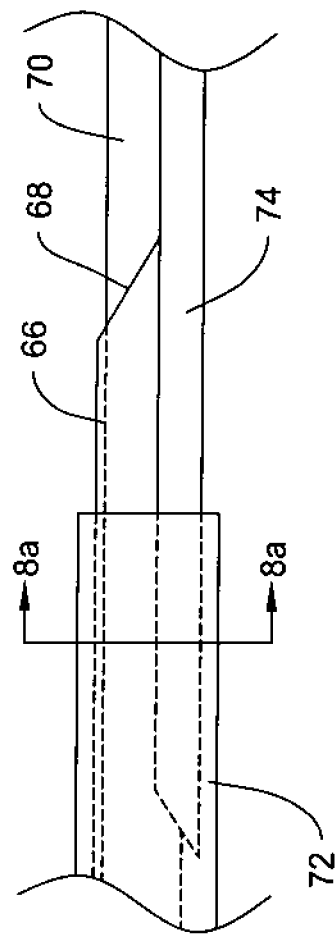

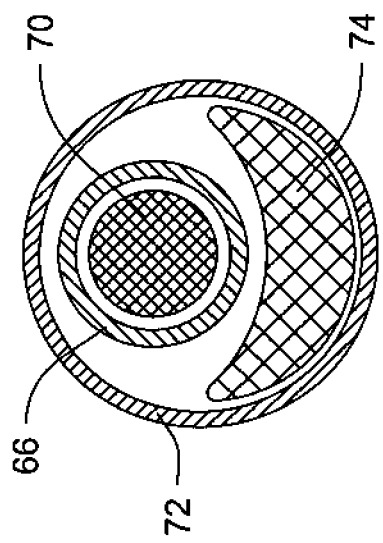
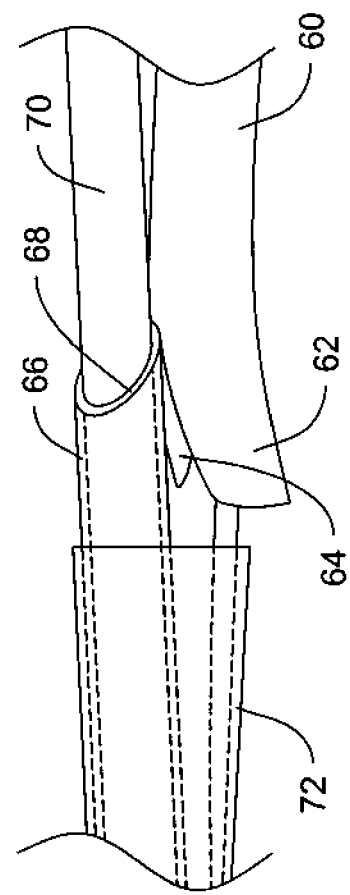

BALLOON CATHETER WITH IMPROVED PUSHABILITY

CROSS REFERENCE TO RELATED APPLICATIONS

This application is a continuation of U.S. application Ser. No. 12/638,318 filed Dec. 15, 2009, now U.S. Pat. No. 8,172,864, which is a continuation of U.S. application Ser. No. 10/436,216, filed May 12, 2003, now U.S. Pat. No. 7,632,288, the entire disclosures of which are incorporated herein in their entirety.

FIELD OF THE INVENTION

The present invention pertains to angioplasty and angioplasty balloon catheters. More particularly, the present invention pertains to angioplasty cutting balloon catheters that include improved pushability

BACKGROUND OF THE INVENTION

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire so that the balloon is positioned adjacent a stenotic lesion. The balloon is then inflated, and the restriction of the vessel is opened. It is typically considered desirable to have a catheter which varies in flexibility along its length, from a stiffer proximal section to a more flexible distal section.

One of the major obstacles in treating coronary artery disease and/or treating blocked blood vessels is restenosis. Evidence has shown that cutting the stenosis, for example with an angioplasty balloon equipped with a cutting blade, during treatment can reduce incidence of re-stenosis in certain applications. Additionally, cutting the stenosis may reduce trauma at the treatment site and/or may reduce the trauma to adjacent healthy tissue. Cutting blades may also be beneficial additions to angioplasty procedures when the targeted occlusion is hardened or calcified. Thus, angioplasty balloons equipped with cutting edges have been developed to attempt to enhance angioplasty treatments.

SUMMARY OF THE INVENTION

The present invention includes catheters adapted for use as rapid exchange angioplasty catheters including features which provide good pushability and kink resistance. In a first embodiment, a rapid exchange cutting balloon angioplasty catheter is provided, the illustrative catheter including a proximal hypotube section which connects to a more distal braided catheter section. The braided catheter section connects to a midshaft portion that includes a guidewire entry port. Each of the hypotube, braided catheter section, and midshaft portion includes at least one inflation lumen for providing fluid communication from a proximal end of the catheter to a distally disposed cutting balloon. Distal of the midshaft portion is a distal section having an inflation lumen and a guidewire lumen, and a cutting balloon is disposed on the distal section in fluid communication with the inflation lumen. In a further illustrative embodiment, a core wire extends across the joint from the hypotube to the braided catheter section and may even extend past the guidewire entry port. The use of a braided catheter section just distal of the hypotube not only allows for a kink-resistant transition but also provides additional pushability for that portion of the shaft, while still adding to the flexibility and softness of the catheter shaft distal of the hypotube.

BRIEF DESCRIPTION OF THE DRAWINGS

FIG. 2 is a cross-sectional side view of an illustrative guidewire entry port;

FIG. 3 is a cross-sectional view taken along line 3-3 in FIG. 2;

FIG. 7 is a top view of an illustrative slit and flared member;

FIG. 8 is a side view showing a step of forming an illustrative port joint;

FIG. 8A is a cross-sectional view taken along line A-A in FIG. 8;

FIG. 9 is a side view showing another step in forming an illustrative port joint;

DETAILED DESCRIPTION OF THE PREFERRED EMBODIMENTS

Figure 1:
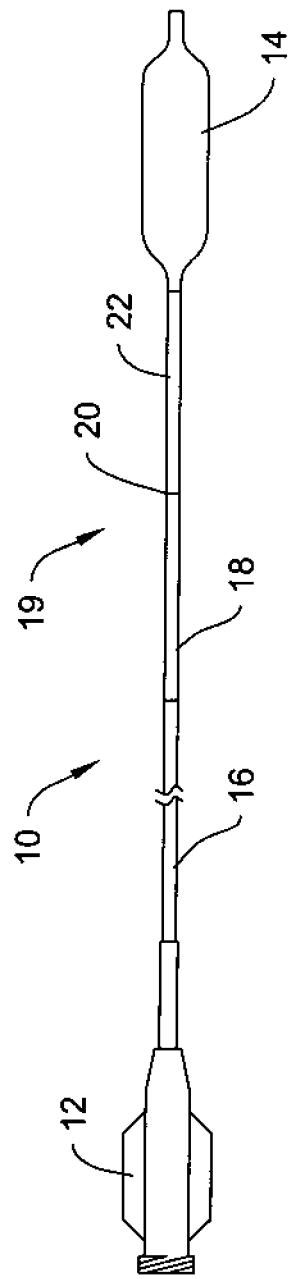
FIG. 1 is a schematic view of a balloon angioplasty catheter.

The following description should be read with reference to the drawings wherein like reference numerals indicate like elements throughout the several views. The drawings, which are not necessarily to scale, depict illustrative embodiments and are not intended to limit the scope of the invention.

FIG. 1 is a schematic view of a balloon angioplasty catheter. The catheter 10 includes a proximal hub assembly 12 and a distal balloon 14 (which may include cutting elements as further illustrated below) with an elongated shaft therebetween. The catheter 10 includes a hypotube 16, a braided member 18 attached to the hypotube 16, a port joint 20, and a distal section 22. The port joint 20 may be considered either a part of the distal section 22 or may be a part of a midshaft 19 that runs between the distal section 22 and the braided member 18, or may be an integral part of the catheter 10.

The hypotube 16 is a thin walled metallic tubular element that is preferably made of stainless steel, though a variety of other materials may also be used, as desired. The hypotube 16 may include a lubricious coating such as a polytetrafluoroethylene coating to reduce frictional resistance. The braided member 18 is attached to the hypotube 16 in a lap joint created by passing the distal end of the hypotube 16 into the braided member 18 by some distance, with an adhesive applied to one, the other, or both of the hypotube 16 and braided member 18. Alternatively, an adhesive may be added after placing the distal end of the hypotube 16 into the braided member 18 by taking advantage of capillary action occurring in the small space therebetween. In other embodiments, heating, welding, or mechanical attachment may also be used to couple the hypotube 16 to the braided member 18. An inflation lumen extends from the hub 12 through the hypotube 16 and into the braided member 18, with the joint between the hypotube 16 and the braided member 18 constructed to maintain the integrity of the inflation lumen.

The braided member 18 may take on a number of forms. Typically the braided member 18 will include a lubricious inner layer and a polymeric outer layer, with a braid composed of a number of filaments or strands braided between the inner and outer layers. A helical, double helical, coiled, or woven member may be used in place of the braid. In one illustrative example, the braid is formed of a flat stainless steel wire of a size 0.00075 inches by 0.003 inches, and is placed between an inner polyimide inner layer having a thickness of about 0.00075 inches and a polyether block amide (PEBAX) outer layer having a thickness of about 0.0015 inches. In this illustrative example, the overall braided member 18 has an inner diameter of about 0.028 inches and an outer diameter of about 0.0355 inches (note that these illustrative values are considered from a point where two strands of the braid cross). The braid may be annealed or soft and in the illustrative example, has a pick count of about 55 using a 16-strand construction. Typically, the braid is wound or formed on a mandrel, slid over the inner layer, and then tightened onto the inner layer, and the outer layer is added over the top. The braid may also be wound directly on the inner layer. Coextrusion of the braid and the inner and outer layers may also be done. The above sizes and materials are merely illustrative of one particular embodiment and are not meant to be limiting.

Other embodiments may use a number of alternative braid materials including, for example, tungsten, Ni—Ti alloys, hardened steel, liquid crystal polymers and other metallic or synthetic materials. Additionally, the pick count and number of strands used may be varied widely depending on the desired final characteristics. It should be noted that there is a trade off where, as pick count increases, pushability also increases but kink-resistance tends to decrease. The braided member 18 provides a transition in flexibility as well as extra kink resistance and pushability from the distal end of the hypotube 16 to more distal portions of the catheter.

Distal of the braided member 18 is a port joint 20 in the midshaft 19. The port joint 20 allows a guidewire to be inserted and carried within the catheter 10 distally from the port joint 20 to at least the balloon 14. In a preferred embodiment, the braided member 18 is used to form a part of the port joint 20. Distal of the port joint 20 is a distal member 22 which includes an inflation lumen as well as a guidewire lumen. It should be noted that proximal of the port joint 20, in a preferred embodiment, the guidewire lumen is not included. There is one more lumen distal of the port joint 20 than there is proximal of the port joint 20.

Figure 4:
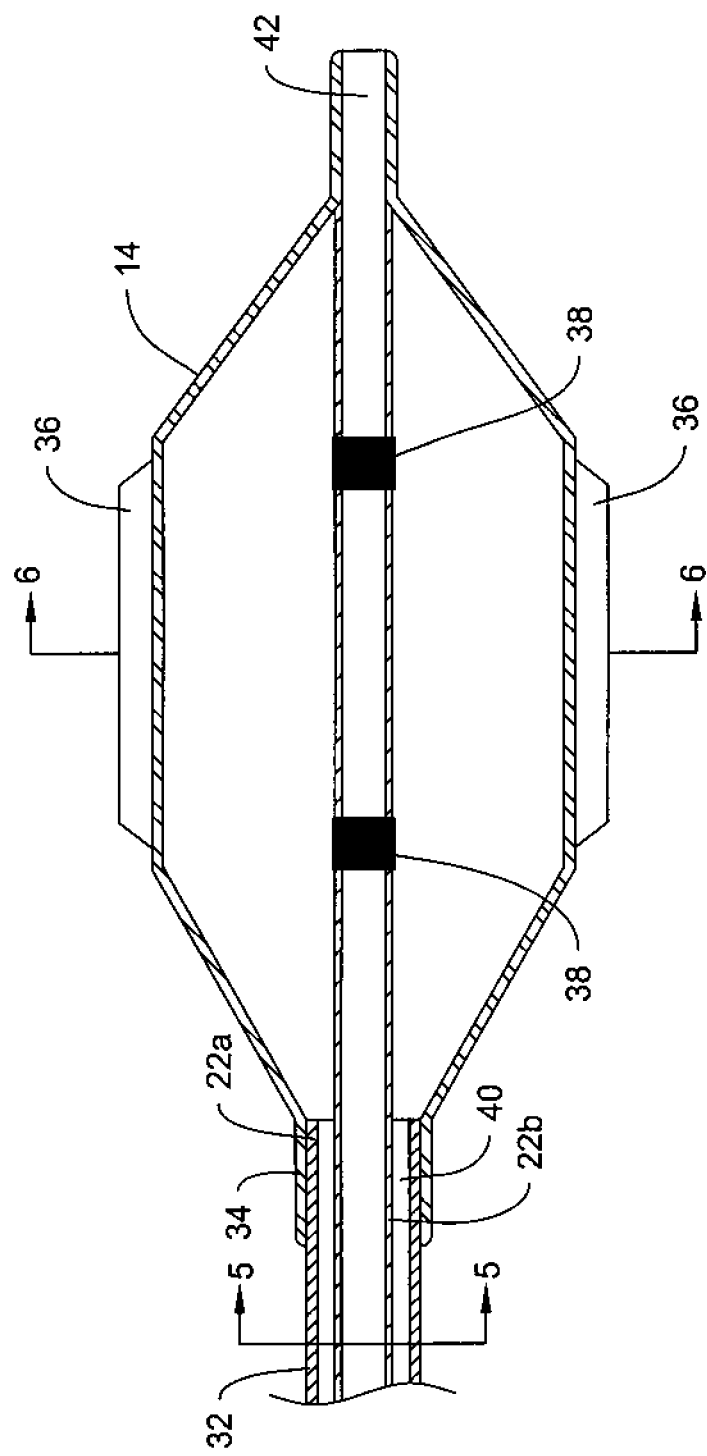
FIG. 4 is a cross-sectional side view of an illustrative cutting balloon.

A balloon 14 is then attached to the distal member 22. In a preferred embodiment the balloon includes a number of cutting members 36, as further illustrated in FIG. 4. The cutting members or cutting blades can include any type of protrusion extending radially from at least a portion of the balloon. Radially projecting longitudinal blades are depicted in FIG. 4. However, cutting blades can be stiffening members, elongated ridges, molded or attached polymeric ridges, polymeric protrusions and combinations thereof.

The use of the braided member 18 may allow several advantages. In one aspect, the catheter pushability is most greatly affected by its weakest member. Distal of the port joint 20, the catheter 10 passes over a guidewire in use, and with a guidewire through the guidewire lumen, the pushability of that section tends to be relatively good. The hypotube 16 is highly pushable. Without the braided member 18, either the hypotube 16 must be longer or a non-braided polymeric member can be used. The length of the hypotube 16, however, is somewhat limited by anatomy of the patient, since the hypotube 16 is ill suited to traverse the more tortuous vasculature nearer the heart. By providing the braided member 18, the hypotube 16 may make up only a more proximal portion of the catheter 10 that does not traverse particularly difficult areas of the vasculature.

FIG. 2 is a cross-sectional side view of an illustrative guidewire entry port. The braided member 18 is illustrated coupled with the distal member 22, which includes both an outer member 22a and an inner member 22b. The braided member 18 is shown having a triple layer configuration, with an outer polymeric layer 18a that is preferably a relatively soft polymer which may include a hydrophilic coating, a braided middle layer 18b having a metallic or non-metallic filament/strand braid, and a lubricious inner layer 18c. In a preferred embodiment, the distal member 22 is made of two integral pieces, an outer member which is a PEBA element and an inner tri-layer member having an inner lubricious layer, a tie layer, and an outer polymer layer. In one embodiment, the inner member 22b is a tri-layer construction including an inner layer of high density polyethylene, an outer layer of PEBA and a tie-layer of a modified low density polyethylene. The port joint 20 allows entry of a guidewire to the inner member 22b at the proximal end of the inner member 22b. An optional core wire 24 is illustrated as crossing the port joint 20 to improve kink resistance across the port joint 20.

The core wire 24 may be provided as a full length core wire extending from the proximal hub (FIG. 1), or may be attached to the proximal hypotube (FIG. 1) section by a suitable method such as brazing or welding. The core wire 24 may attach to the hypotube 16 by crimping the hypotube 16 to surround and attach to the core wire 24 or the proximal end of the core wire 24 may extend into this distal end of the hypotube 16 lumen and be affixed therein.

It should be noted that while the members 18, 22a, 22a are illustrated as separate pieces, in some embodiments a port joint 20 may be constructed using a heating process (such as that discussed with reference to FIGS. 7-10A below and as shown in cross section in FIG. 3) that causes reflow of various elements such that sharp distinction of the several members 18, 22a, 22b no longer exists in an actual fabricated catheter. The port joint 20 may be constructed by any suitable fashion, and that discussed below is only provided for illustrative purposes.

FIG. 3 is a cross-sectional view taken along like 3-3 in FIG. 2. A guidewire lumen 30 is provided through the portion distal of the port joint 20 (FIG. 1). The core wire 24 is seen to sit within an inflation lumen 28. The shape of the inflation lumen 28 near the port joint 20 is illustrated in accordance with the illustrative port joint discussed in FIGS. 7-11. Lumens having other shapes may also be used, as desired. As noted above, the illustrative port joint of FIG. 3 has been constructed so that the several elements used in making the port joint are no longer clearly discerned. The cross section includes areas of double cross hatching 18b to indicate that a portion of the braided member 18b stands out from what is otherwise a melted-together blend of polymers.

FIG. 4 is a cross-sectional side view of an illustrative cutting balloon shown in an inflated configuration. The cutting balloon 14 is attached at its distal end 32 to the inner member 22b, and at its proximal end 34 to the outer member 22a. This leaves the interior of the cutting balloon 14 in fluid communication with a generally annular inflation lumen 40 defined between the outer member 22a and the inner member 22b. The balloon 14 may be attached using heat welding processes, adhesives, or a heat shrink wrapping, for example. Two marker bands 38 are included on the inner member 22b to aid in visualizing the location of the balloon 14 in the vasculature. The balloon 14 may be made from typical angioplasty balloon materials including, for example, polymers or blends of polymers such as polyethylene terephthalate (PET), polyetherimide (PEI), and/or polyethylene (PE).

On the surface of the balloon 14 are a number of cutting elements 36. The cutting elements 36 may be disposed in any configuration including, for example, two, four or six equally spaced cutting elements 36. The cutting elements 36 may be blades or other structures configured for cutting into plaque or tissue such as a lesion. While the cutting elements 36 may be made of metal, the exact composition of the cutting elements 36 may vary and may include, for example, hard, flexible plastics. In use, when the balloon 14 is inflated, the cutting elements 36 create cuts in surrounding tissue, lesions, or plaque. These cuts are believed to create scoring that improves removal of a blockage and also reduces the occurrence of re-stenosis.

The inner member 22b extends through the balloon 14 to the distal tip of the catheter. A guidewire lumen 42 through the inner member 22b allows the balloon 14 and catheter to be advanced over a guidewire which passes through guidewire lumen 42 of the inner member 22b.

Figure 5:
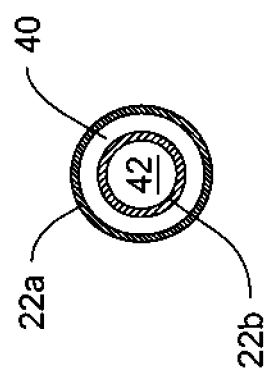
FIG. 5 is a cross-sectional view taken along line 5-5 in FIG. 4.

FIG. 5 is a cross-sectional view taken along line 5-5 in FIG. 4. As shown in FIG. 5, the outer member 22a surrounds the inner member 22b such that a generally annular inflation lumen 40 is defined therebetween. This inflation lumen 40 is in fluid communication with the balloon as well as the proximal end of the catheter, and is used for allowing an inflation fluid to be passed into the catheter, through several proximal elements, through the annular lumen, and into a balloon at the distal end. The inner member 22b defines a guidewire lumen 42.

Figure 6:
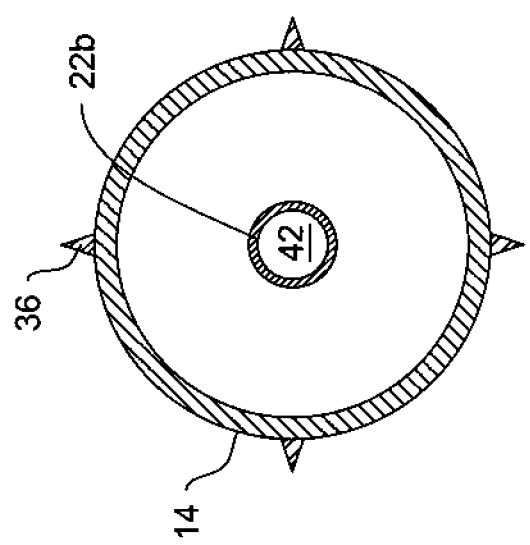
FIG. 6 is a cross-sectional view taken along line 6-6 in FIG. 4.

FIG. 6 is a cross-sectional view taken along line 6-6 in FIG. 4. It can be seen that the cutting elements 36 extend out from the outer surface of the balloon 14. It should be noted that the several Figures are not necessarily to scale. The guidewire lumen 42 is separated from the interior of the balloon by the inner member 22b.

FIGS. 7-10 are provided to show an illustrative "slit and flare" method for forming a port joint in a catheter such as the port joint 20 illustrated in FIG. 2. This illustrative method is provided merely to allow one skilled in the art to practice the invention. However, other methods for producing a port joint may also be used. Instead of a slit and flare method, for example, a proximal member may be crimped to create a guidewire entry location, and a guidewire receiving tubular element provided distal of the crimp.

FIG. 7 is a top view of an illustrative slit and flared midshaft member. The midshaft member 60 is preferably a multilayer shaft with a braid or other support structure. In FIG. 7, the braid is not shown to aid in depicting the joint. As can be seen, one end of the midshaft member 60 has been slit and flared to create a flared portion 62 and a tab 64. The midshaft member 60 is used as noted below with respect to FIG. 10. A mandrel (not shown) having a crescent shaped end is loaded through the midshaft member 60 with the crescent end passing out through the slit and flared end of the midshaft member 60.

FIG. 8 is a side view showing a step of forming an illustrative port joint. An inner member 66 has been skived at one end at an angle of about 60 degrees. For the illustrative port joint, the inner member is a tri-layer design having a lubricious inner polymer layer (preferably a high density polyethylene), a tie layer, and a poly-ether block amide (PEBA) outer layer, where the tie layer is used in the conventional manner to allow the lubricious inner layer to adhere to the PEBA outer layer. Other lubricious materials, tie layers, and outer layers may be used as desired. The skive 68 is shaped to enable ready fabrication of a guidewire entry port, with the guidewire entering through the skive 68. The inner member 66 is shown with an inner mandrel 70 extending through the skive 68. The inner member 66 is loaded through an outer member 72 until the skive 68 passes out of the outer member 72.

A crescent mandrel 74 is illustrated as passing into the outer member 72. The crescent mandrel 74 includes a curved "bed" which allows it to pass between the inner member 66 and the outer member 72, with one side of the curved area of the crescent mandrel 74 generally matching the inner wall of the outer member 72. The other side of the curved area is shaped to match the outer wall of the inner member 66. The skive 68 is aligned to open facing away from the crescent mandrel 74.

FIG. 8A is a cross sectional view taken along line A-A in FIG. 8. As can be seen from FIG. 8A, the curved portion of the crescent mandrel 74 is shaped to slide in between the inner member 66 and the outer member 72. There is some amount of extra space allowed, which is used to receive the tab 64 (FIG. 7) of the midshaft member 60 (FIG. 7), as further illustrated below in FIGS. 10-10A. The other mandrel 70 is illustrated in place for maintaining the shape and position of the inner member 66 during subsequent placement, shrink wrapping, and laser welding processes.

FIG. 9 is a side view showing another step in forming an illustrative port joint. With the crescent mandrel 74 placed as illustrated in FIG. 8, the midshaft member 60 is slid toward the distal inner member 66 and distal outer member 72. The tab 64 is placed between the distal inner member 66 and the crescent mandrel 74. For the illustrative method, the tab is only about 1.25 millimeters long, while the crescent mandrel 74 extends about 8 millimeters into the distal outer member 72, so the crescent mandrel 74 prevents the tab 64 from touching the distal outer member 72. The short side of the distal inner member 66 extends about 1 millimeter past the end of the distal outer member.

Figure 10:
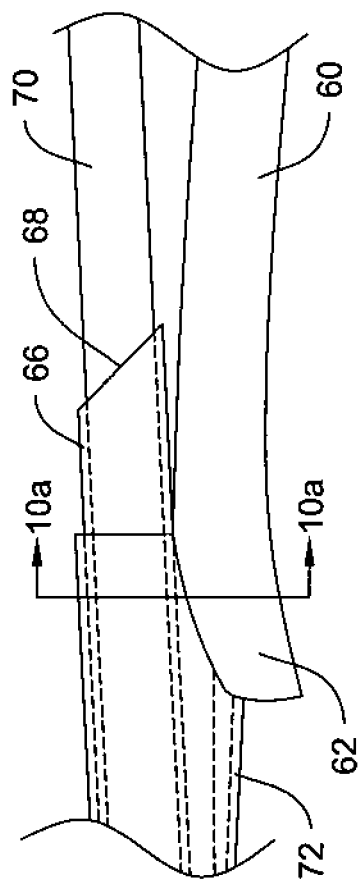
FIG. 10 is a side view showing yet another step in forming an illustrative port joint.

FIG. 10 is a side view showing yet another step in forming an illustrative port joint. After the configuration of FIG. 9 is achieved, with the tab 64 (not shown) properly placed as explained, the midshaft member 60 is slid over the crescent mandrel 74 until the slits that define the tab 64 (not shown) bottom out against the outer member 72. The flared portion 62 is placed to partially surround the distal outer member 72.

Figure 10A:
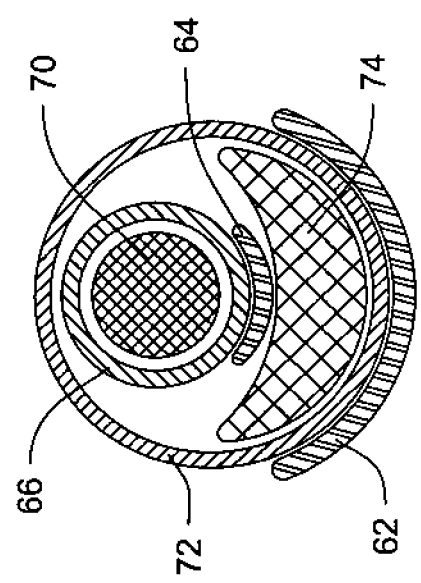
FIG. 10A is a cross-sectional view taken along line A-A in FIG. 10.

FIG. 10A is a cross-sectional view taken along line A-A in FIG. 10. As illustrated, the crescent mandrel 74 sits between the outer member 72 and the tab 64 of the midshaft member 60. The tab 64 sits against the inner member 66, while the inner member sits against the outer member 72 on its other side.

Once in the configuration of FIGS. 10-10A, a heat shrink member is placed over the port joint to secure the various elements in place. Then a laser heating process is used to cause reflow and fusion between the several pieces. The heat shrink member and mandrels are then removed, and the finished port joint subassembly is used as a component of a catheter such as the catheter 10 of FIG. 1. The finished port joint subassembly may be treated to trim any residual pieces from the heating process. Also, in some methods, the port joint is skived or trimmed so that a part of the inner member 66 is removed to create a smooth, well controlled and well defined guidewire entry location.

It should be noted that in an alternative embodiment, an additional polymeric member may be used. For example, referring to FIG. 1, a polymeric member lacking an inner braid may be provided between the port joint 20 and the braided member 18, with the polymeric member included to make the fabrication of a slit and flared member for use in the port joint 20 easier. In another embodiment, the port joint 20 may be provided as a discrete component having a polymeric member, which may include a simple single layer construction or may be more complicated and include a braid or special tri-layer design. The polymeric member may extend proximally and connect to the braided member 18.

Those skilled in the art will recognize that the present invention may be manifested in a variety of forms other than the specific embodiments described herein. Accordingly, departures in form and detail may be made without departing from the scope and spirit of the present invention as described in the appended claims.

What is claimed is:

1. A rapid exchange catheter comprising:
    an elongated shaft having a proximal end and a distal end, the elongated shaft including:
        a hypotube having a proximal end and a distal end;
        a midshaft portion having a proximal end and a distal end, the midshaft portion being attached near its proximal end to a location near the distal end of the hypotube, the midshaft portion including a braided member; and
        a distal portion including an inner tubular member and an outer tubular member surrounding the inner tubular member, a short guidewire lumen being defined by the inner tubular member and an inflation lumen being defined between the inner tubular member and the outer tubular member, the distal portion being attached to the midshaft portion and extending distally therefrom;
        wherein the midshaft portion includes a flared portion and a tab prior to being attached to the distal portion such that when the midshaft portion and the distal portion are attached at an attachment location, a first portion of the braided member is disposed radially exterior to an outer surface of the outer tubular member, and the tab including a second portion of the braided member is disposed between the inner tubular member and the outer tubular member;
    a balloon disposed near the distal end of the elongated shaft; and
    a core wire attached to the hypotube and extending distally of the distal end of the hypotube and across the location at which the proximal end of the midshaft portion is attached to the distal end of the hypotube.

2. The rapid exchange catheter of claim 1, wherein a proximal guidewire port providing entry into the guidewire lumen is formed proximate the attachment location.

3. The rapid exchange catheter of claim 2, wherein the core wire extends distally beyond the proximal guidewire port.

4. The rapid exchange catheter of claim 1, wherein the midshaft portion includes a first polymer layer surrounding the braided member and a second polymer layer disposed within the braid.

5. The rapid exchange catheter of claim 1, wherein the braided member is disposed about a lubricious inner layer.

6. The rapid exchange catheter of claim 5, wherein the midshaft portion includes a polymeric outer layer disposed over the braided member.

7. The rapid exchange catheter of claim 5, wherein the lubricious inner layer includes polyimide.

8. The rapid exchange catheter of claim 1, wherein the core wire is tapered.

9. The rapid exchange catheter of claim 1, wherein the hypotube includes a crimp to attach the core wire to the hypotube.

* * * * *